United States Patent
Logan

(10) Patent No.: US 8,240,066 B2
(45) Date of Patent: Aug. 14, 2012

(54) ARCH SUPPORT INDEPENDENT OF FOOTWEAR

(76) Inventor: Brent Ellis Logan, Mount Vernon, WA (US)

(*) Notice: Subject to any disclaimer, the term of this patent is extended or adjusted under 35 U.S.C. 154(b) by 798 days.

(21) Appl. No.: 11/811,575

(22) Filed: Jun. 11, 2007

(65) Prior Publication Data
US 2007/0283597 A1   Dec. 13, 2007

Related U.S. Application Data

(60) Provisional application No. 60/812,909, filed on Jun. 13, 2006.

(51) Int. Cl.
*A43B 3/12* (2006.01)
*A61F 5/30* (2006.01)

(52) U.S. Cl. .................... 36/91; 36/145; 602/66

(58) Field of Classification Search ............. 36/89, 91, 36/145, 11.5, 88, 8.1, 4, 50.1, 51, 58.5, 58.6, 36/72 R, 7.3, 59 C, 103, 113, 76 R; 602/66
See application file for complete search history.

(56) References Cited

U.S. PATENT DOCUMENTS

| | | | | |
|---|---|---|---|---|
| 987,599 A * | 3/1911 | Quenzer | ........................ | 602/66 |
| 1,091,931 A * | 3/1914 | Harris | ........................ | 602/66 |
| 1,318,972 A * | 10/1919 | Cook | ........................ | 602/66 |
| 1,443,844 A * | 1/1923 | Jensen | ........................ | 602/66 |
| 1,492,514 A * | 4/1924 | Jensen | ........................ | 602/66 |
| 1,627,596 A * | 5/1927 | Cutshaw | ........................ | 602/66 |
| 1,651,285 A * | 11/1927 | Levick, Jr. | ........................ | 602/66 |
| 2,358,966 A * | 9/1944 | Einstoss | ........................ | 602/66 |
| 5,545,129 A * | 8/1996 | Snook | ........................ | 602/66 |
| 5,607,756 A * | 3/1997 | Yamauchi et al. | ........................ | 442/6 |
| 5,840,053 A * | 11/1998 | Roth | ........................ | 602/66 |
| 7,041,075 B2 | 5/2006 | Sullivan | | |
| 7,055,265 B1 | 6/2006 | Bathum et al. | | |
| 7,121,020 B1 | 10/2006 | Bathum | | |

* cited by examiner

*Primary Examiner* — Jila M Mohandesi
(74) *Attorney, Agent, or Firm* — Dwayne E. Rogge; Schacht Law Office, Inc.

(57) ABSTRACT

This device elevates the midsection of the foot when shoeless, addressing congenital flatness, or lapsing or pronation in the arch. The device, which can be constructed of various materials, does not support the metatarsus or heel, and is attached to the foot by lateral straps or equivalents. The device may be worn inside or over stockings. The device can also serve as an orthotic for barefoot runners or dancers by means of longitudinal extension, with openings under the metatarsus and heel so these areas may touch the ground or floor. This device may be contraindicated as a diagnostic or therapeutic aid, without the intent of medical application.

4 Claims, 5 Drawing Sheets

ARCH SUPPORT INDEPENDENT OF FOOTWEAR

REFERENCES CITED

U.S. Patent Documents

| | | |
|---|---|---|
| 7,041,075 | May 2006 | Sullivan |
| 7,055,265 | June 2006 | Bathum |
| 7,121,020 | October 2006 | Bathum |

CROSS-REFERENCE TO RELATED APPLICATIONS

This application claims the benefit of U.S. Provisional Patent Application No. 60/812,909 having a filing date of Jun. 13, 2006, the primary contents of which are hereby incorporated by reference.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

Flat feet, whether congenital, from fallen arches, or pronated by lateral deformation inward or outward, afflict sometimes excruciating pain for approximately 30 percent of the human population, including a substantial urban increase due to recent weight gains from highly caloric diets, and in developed countries are alleviated by footwear orthotics such as arch supports or insoles of various designs and materials. But once the user is inside a home or in an informal outdoor environment, shoe inserts are typically removed, against podiatric advice, along with footwear as relaxation is sought or cultural practices observed, with alternatives being stockings, slippers, moccasins, or simply bare feet. However, physical or psychological reliance upon arch supports remains, and that unaddressed dependency is the tradeoff for freedom from the constraints of workplace foot attire. To resolve this dilemma, an independent orthotic, as distinguished from a temporary brace or bandage, without the necessity of its placement requiring footwear, centered on the instep and which leaves free the toes, metatarsus, and heel, would be a desirable innovation, one rapidly becoming essential for relief. Prototype testing has shown that even individuals without arch problems find this invention comfortable, supportive, and an aid to traction indoors or out, on rough along with smooth surfaces, thereby inaugurating an entirely new category of general footwear as well as a specialized orthotic. As listed in the U.S. Patent Documents above, several devices for supporting barefoot athletic activity, such as running or dancing, are known to the art, but these physically extend to the heel, toes, or both, and some are merely attached to the foot by wrappings of various materials, while none is intended or designed for normative household or ambulatory comfort, although this invention may be novelly adapted to more mobile purpose, with two such configurations given.

BRIEF SUMMARY OF THE INVENTION

This nonmedical device is a safe, effective, unique, and lowcost means for alleviating instep pain due to flat feet, fallen arches, or pronation by providing a comfortable contour and relaxing pressure when walking or standing barefoot on hard surfaces. A shoeless arch support constructed of any appropriate material, such as rubber, plastic, polymer foam, fabric, gel cushion, etc., with surfaces treaded to prevent epidermal slipping and aid ground traction, can be affixed directly to the foot with one or more continuous tension straps or bands of diverse composition, such as elastic, fabric, leather, rubber, polyester, etc., or adjustable halves fastening for foot size by velcro, snap, buckle, or other means, and may feature an ankle strap or band for additional security. This innovation is to be utilized without footwear, or inside or over stockings. User sizes as well as arch elevation can be various. An identical round or oval shape defining each support permits the pair to be worn interchangably, thus avoiding confusion over which is intended for the left or right foot. While the sole features a slight grid against undersurface slippage, deeper treads for outdoor use in or out of water would be appropriate. Design variations may include any color, texture, contour, wording, decorative jewelry or beads. Unlike conventional shoe inserts, these supports would not extend significantly past the arch in any direction, neither under the heel or ball of the foot, but cover only the midsection of the sole, and therefore could be considered a partial or abbreviated orthotic sandal with tapered longitudinal ends. A slightly raised lip on both lateral sides of each support deters twisting or slippage, particularly important in a humid climate or water, as does texturing of the surface which touches the epidermis of the foot. Construction should be sufficient to permit machine washability and drying.

BRIEF DESCRIPTION OF THE SEVERAL VIEWS OF THE DRAWINGS

The unique features that are characteristic of the present invention are set forth in the appended claims. However, the preferred embodiments of the invention, together with further objects and attendant advantages, are best understood by reference to the following detailed description taken in connection with the accompanying drawings in which:

DETAILED DESCRIPTION OF THE INVENTION

Figure 1:
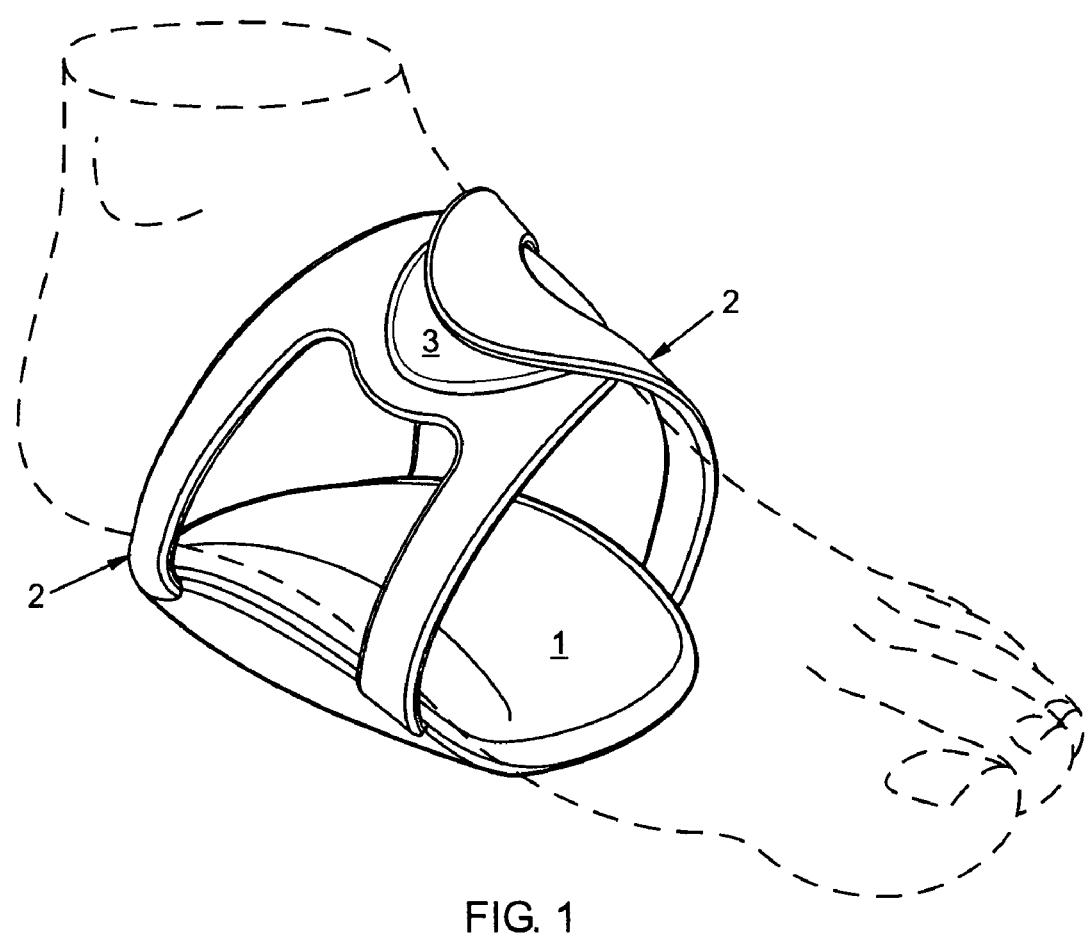
FIG. 1 is a ¾ frontal perspective view of the device positioned on a left foot depicting an arch support elevated on the right instep of the foot, and extending longitudinally not beyond the midsole, leaving the metatarsus, toes, and heels uncovered, with two lateral support straps surrounding the foot and fastened where they meet at the top by an adjustable clip, snap closure, velcro, or other such means.
Figure 1A:
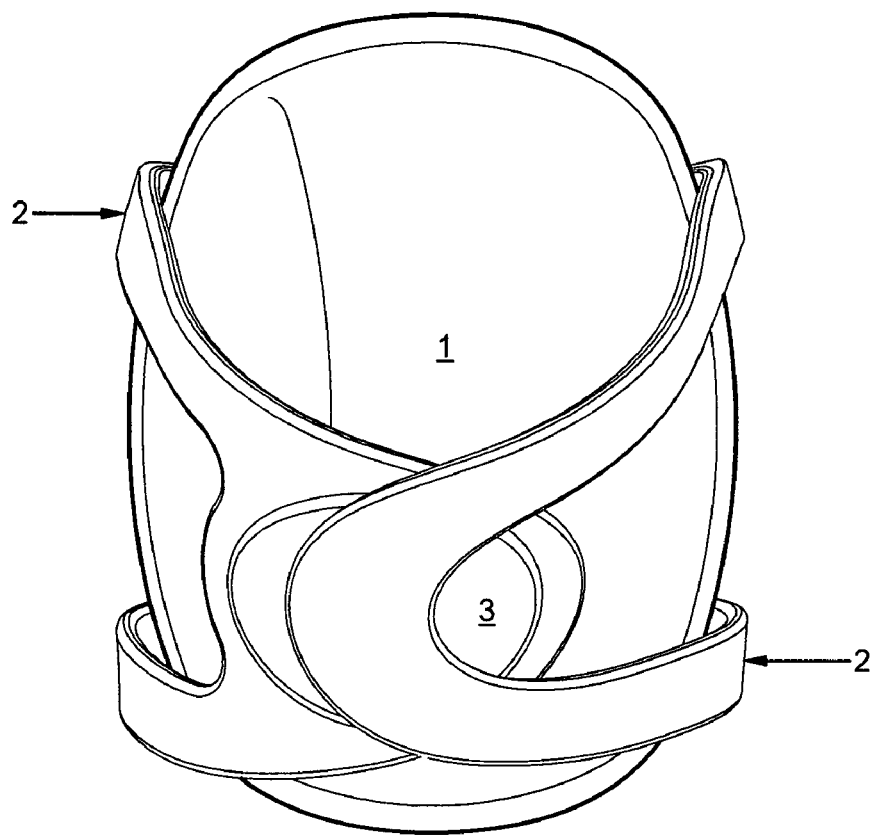
FIG. 1A is a top perspective view of the device alone, with its raised arch support depicted here on the left side which by reversing the longitudinal position of the invention can be worn without other alteration on the opposing foot, showing two lateral support straps directly attached to the sole, and surrounding the foot and attached where they meet at the top by an adjustable clip, snap closure, velcro, or similar fastener.
Figure 1B:
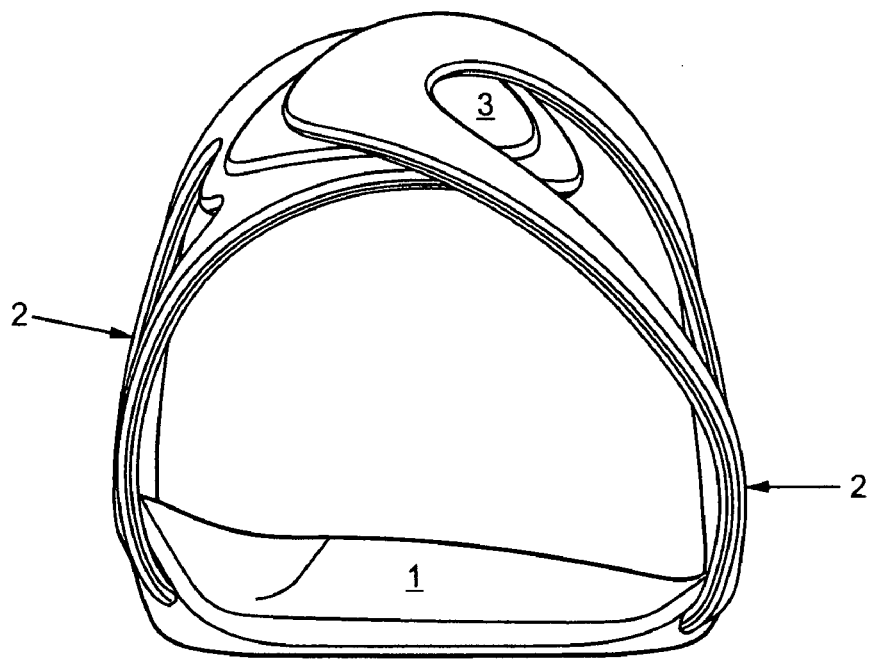
FIG. 1B is a front or back perspective view of the device alone, with its raised arch support depicted here on the left side which by reversing the longitudinal position of the invention can be worn without other alteration on the opposing foot, showing two lateral support straps directly attached to the sole, and surrounding the foot and joined where they meet at the top by an adjustable clip, snap fitting, velcro, or like closure.
Figure 1C:
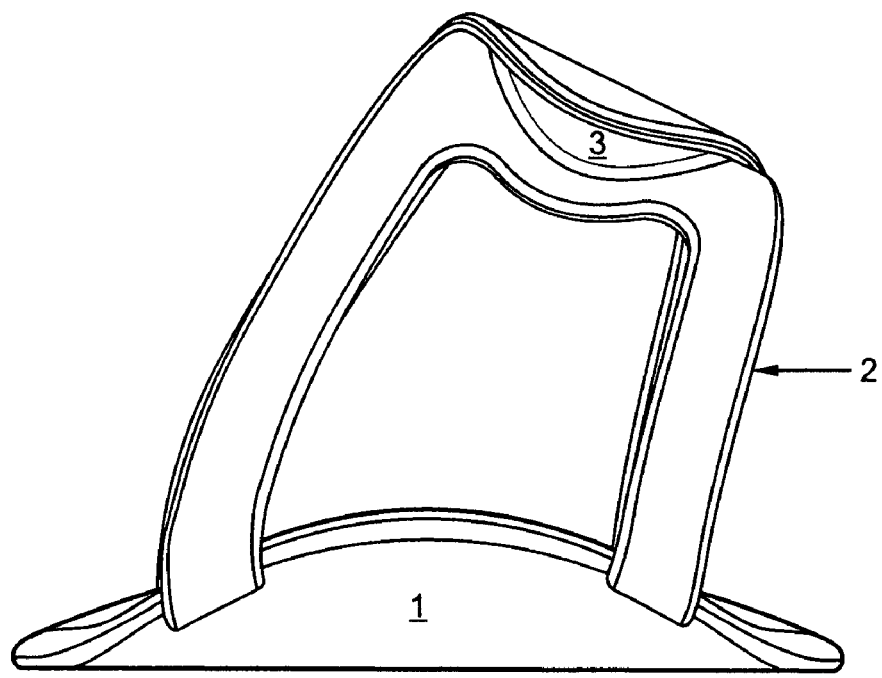
FIG. 1C is a side perspective view of the device alone, depicted from the right as if positioned on either foot therefore its lateral support straps incline toward the right or front of each foot, said strap angle reversing were the devices exchanged for wearing on the opposite foot, as adjusted by the top strap fasteners.
Figure 1D:
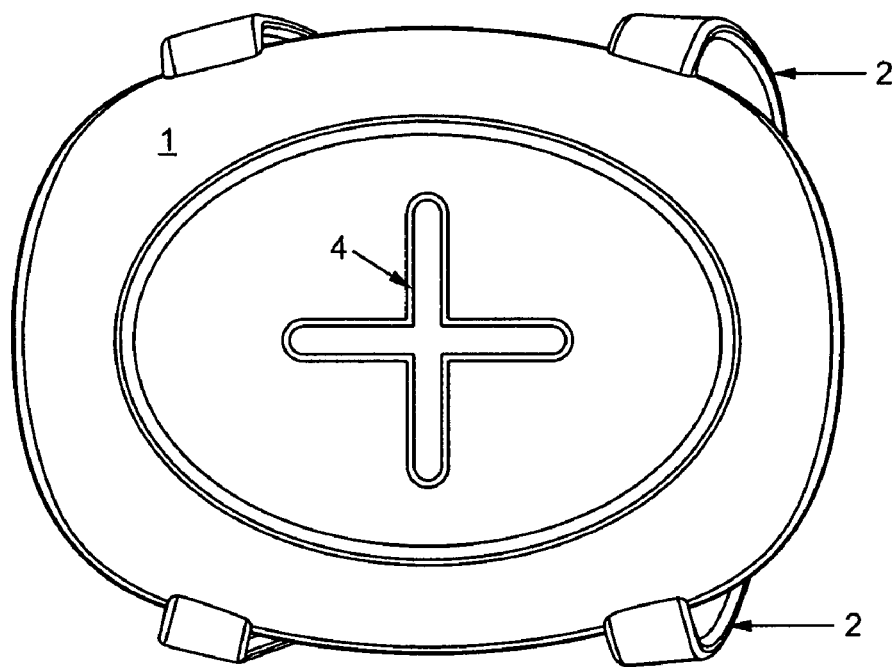
FIG. 1D is a bottom or underside perspective view of the device alone, illustrating how in an approximately round or oval shape it does not extend longitudinally past the midsole, leaving the metatarsus, toes, and heels free, with two lateral support strap or band ends depicted where they attach to the arched base, and a textured underside design to deter ground or floor slippage.

Referring to FIG. 1, one embodiment of the present device in a ¾ frontal perspective illustrates on a left foot an arch support, 1, elevated on the right instep of the foot, and extending longitudinally not beyond the midsole, leaving the metatarsus, toes, and heels uncovered, with two lateral support straps, 2, surrounding the foot and fastened where they meet at the top, 3, by an adjustable clip, snap closure, velcro, or other such means. FIG. 1A represents a top perspective view of the device alone, with its raised arch support, 1, depicted here on the left side which by reversing the longitudinal position of the invention can be worn without other alteration on the opposing foot, showing two lateral support straps, 2, directly attached to the sole, and surrounding the foot and joined where they meet at the top, 3, by an adjustable clip, snap closure, velcro, or similar fastener. FIG. 1B depicts a front or back perspective view of the device alone, with its raised arch support, 1, portrayed here on the left side which by reversing the longitudinal position of the invention can be worn without other alteration on the opposing foot, showing two lateral support straps, 2, directly attached to the sole, and surrounding the foot and joined where they meet at the top, 3, by an adjustable clip, snap fitting, velcro, or like closure. FIG. 1C illustrates a side perspective view of the device alone, with its arch support, 1, depicted from the right as if positioned on either foot therefore its lateral support straps, 2, incline toward the right or front of each foot, said strap angle reversing were the devices exchanged for wearing on the opposite foot, as adjusted by the top strap fasteners, 3. FIG. 1D shows a bottom or underside perspective view of the device alone, depicting how in an approximately round or oval shape it does not extend longitudinally past the midsole, leaving the metatarsus, toes, and heels free, with two lateral support straps or bands, 2, depicted where they attach to the arched base, 1, and a textured underside design, 4, to deter ground or floor slippage.

Figure 2:
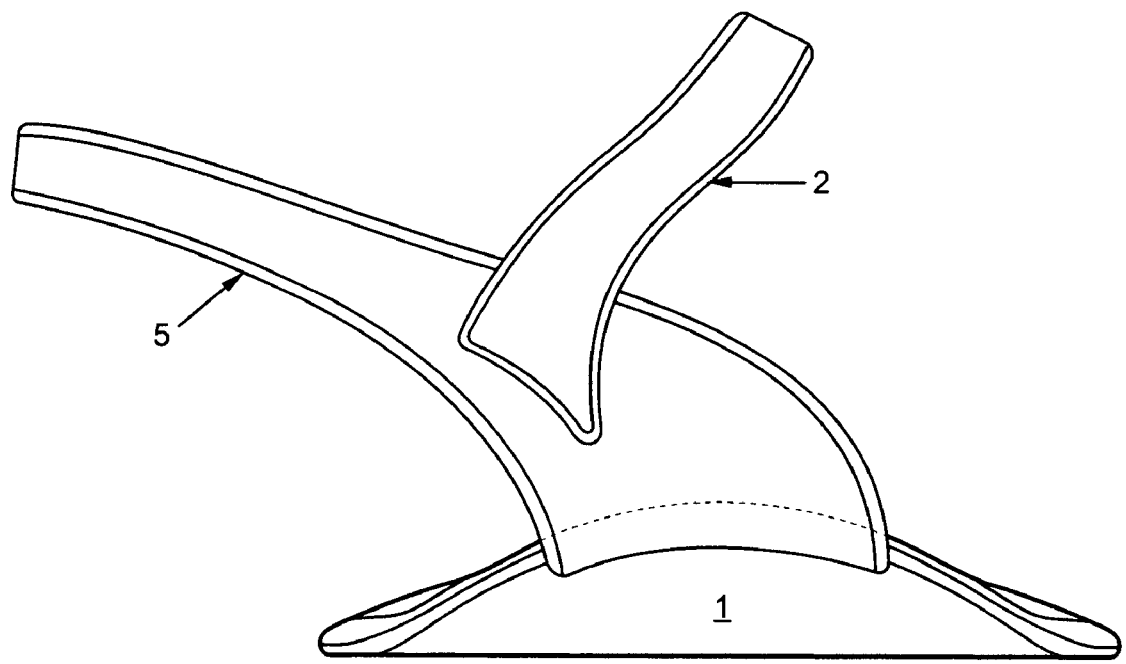
FIG. 2 is a side perspective view of the device alone, depicting an added ankle or heel strap or stretchable band thereby permitting greater user mobility.
Figure 2A:
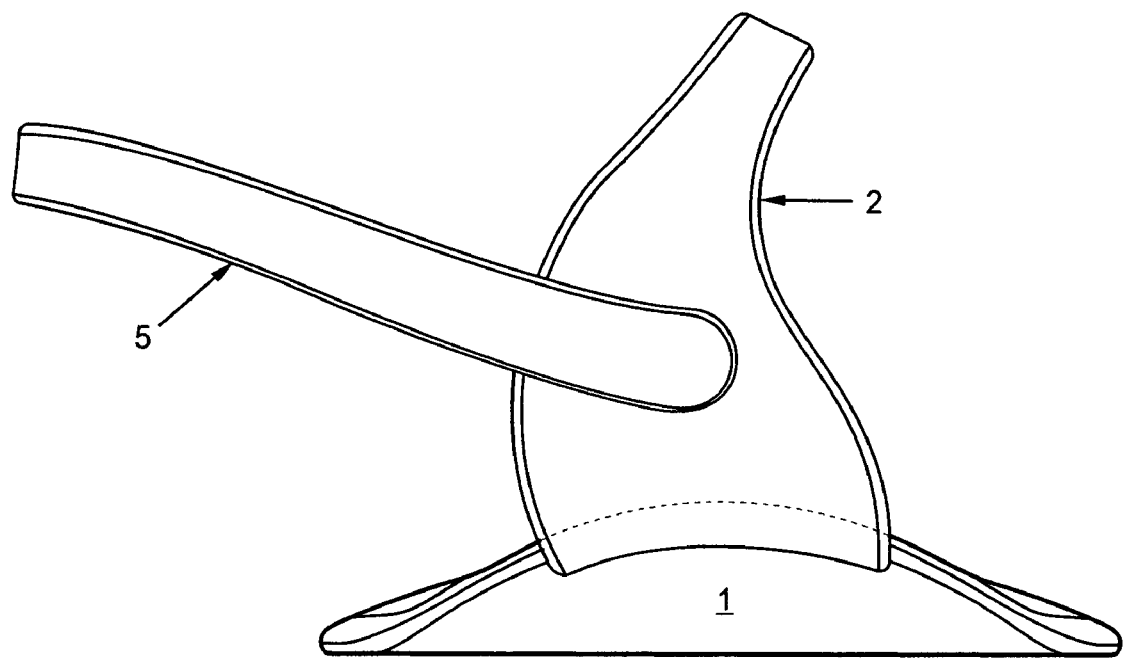
FIG. 2A is a side perspective of the device alone, showing another configuration of an ankle or heel strap or stretchable band thereby increasing athletic capability.

FIG. 2 represents a side perspective view of the device alone, depicting an added ankle or heel strap or stretchable band, 5, connected directly to the arch support, 1, and here attached to the midfoot strap, 2, thereby permitting greater user mobility. FIG. 2A shows a side perspective view of the device alone, with another configuration of an ankle or heel strap or stretchable band, 5, affixed to the midfoot strap, 2, bonded directly to the arch support, 1, thereby increasing athletic capability.

Figure 3:
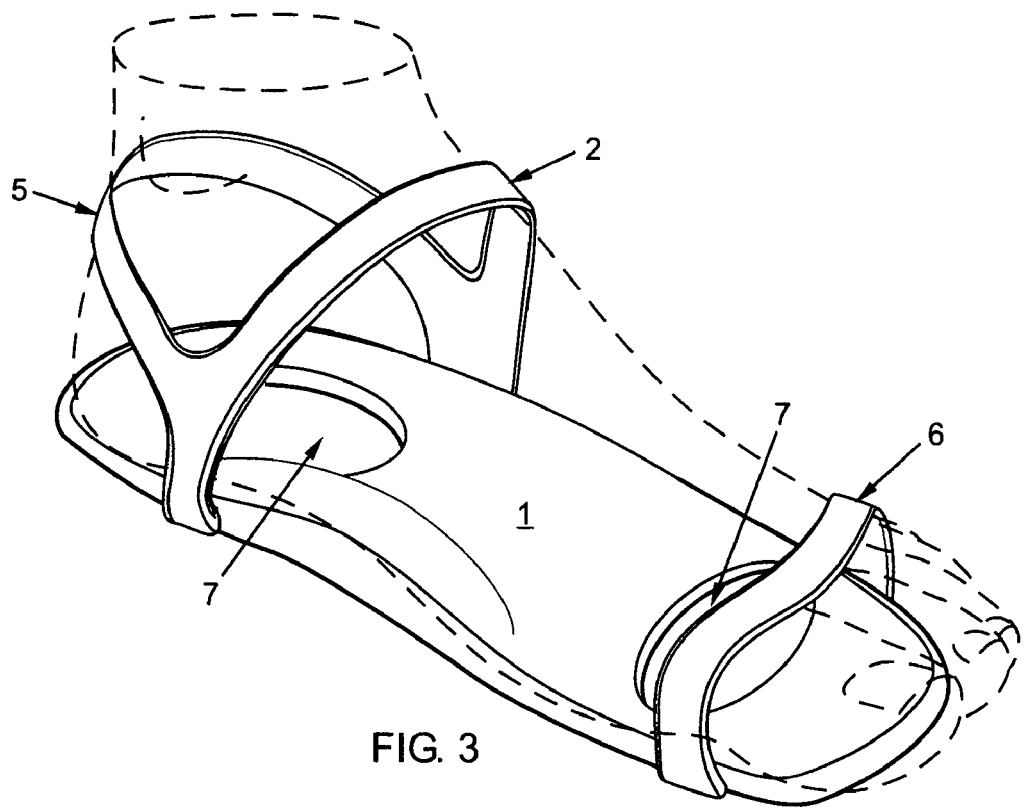
FIG. 3 is a ¾ frontal perspective view of the device positioned on a left foot, extending longitudinally to the front and back of same, with openings in the sole at the metatarsus and heel areas so the epidermis of the foot may touch the ground or floor while retaining an arch support thereby affording enhanced athletic purpose, said invention with lateral attachment to the foot by directly connected straps or, as depicted, stretchable bands of diverse composition, affixed directly at the sole, either as a continuous piece or halves joined by a snap, buckle, velcro or similar fastener, and adding a like ankle or heel strap or band if further foot stability is desired.
Figure 3A:
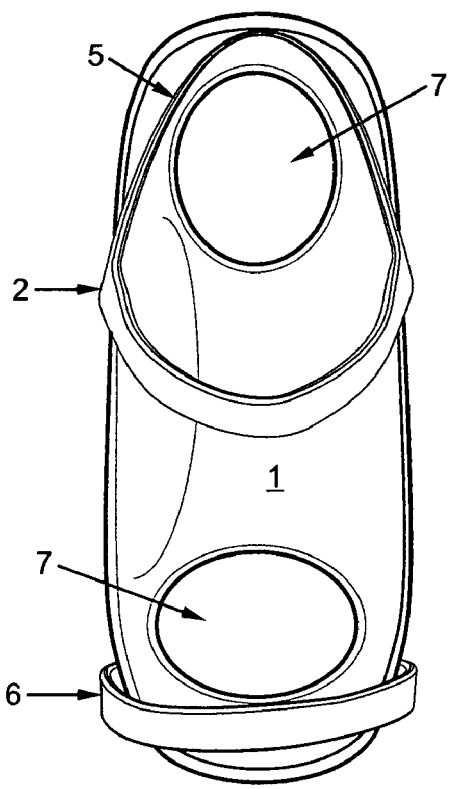
FIG. 3A is a top perspective view of the device alone showing longitudinal extension to the front and back of the foot, with openings in the sole at the metatarsus and heel areas so the epidermis of the foot may touch the ground or floor while retaining an arch support thereby affording enhanced athletic purpose, said invention with lateral attachment to the foot by directly connected straps or, as depicted, stretchable bands of diverse composition, affixed directly at the sole, either as a continuous piece or halves joined by a snap, buckle, velcro or similar fastener, and adding a like ankle or heel strap or band if further foot stability is desired.
Figure 3B:
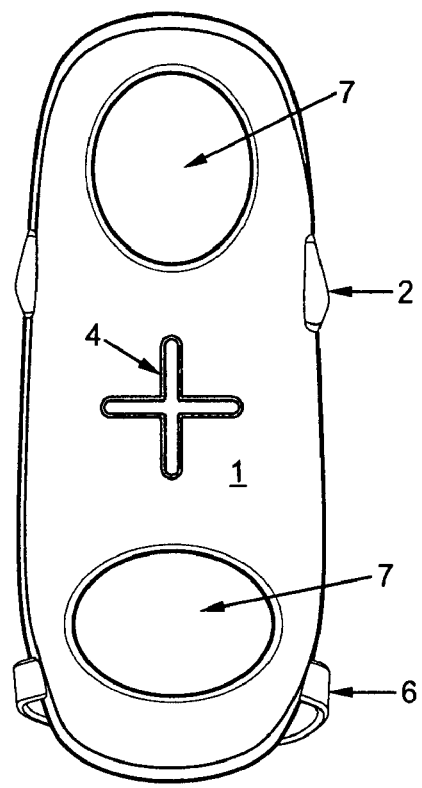
FIG. 3B is a bottom or underside perspective of the device alone illustrating longitudinal extension to the front and back of the foot, with openings in the sole at the metatarsus and heel areas so the epidermis of the foot may touch the ground or floor while retaining an arch support thereby affording enhanced athletic purpose, said invention with lateral attachment to the foot by straps or bands, their direct connection points to the sole shown, and a textured underside design to deter ground or floor slippage.

FIG. 3 depicts a ¾ frontal perspective view of the device positioned on a left foot, extending longitudinally to the front and back of same, with openings, 7, in the sole at the metatarsus and heel areas so the epidermis of the foot touches the ground or floor while retaining an arch support, 1, thereby affording enhanced athletic purpose, said invention with lateral attachment to the foot by directly connected straps, or, as shown, stretchable bands, 2, 6, of diverse composition, affixed directly at the sole, either as a continuous piece or halves joined by a snap, buckle, velcro or similar fastener, and adding an ankle or heel strap or band, 5, if further foot stability is desired. FIG. 3A illustrates a top perspective view of the device alone showing longitudinal extension to the front and back of the foot, with openings, 7, in the sole at the metatarsus and heel areas so the epidermis of the foot may touch the ground or floor while retaining an arch support, 1, thereby affording enhanced athletic purpose, said invention with lateral attachment to the foot by directly connected straps or, as portrayed, stretchable bands, 2, 6, of diverse composition, affixed directly at the sole, either as a continuous piece or halves joined by a snap, buckle, velcro or similar fastener, and adding a like ankle or heel strap or band, 5, if further foot stability is desired. FIG. 3B shows a bottom or underside perspective view of the device alone illustrating longitudinal extension to the front and back of the foot, with openings, 7, in the sole at the metatarsus and heel areas so the epidermis of the foot may touch the ground or floor while retaining an arch support, 1, thereby affording enhanced athletic purpose, said invention with lateral attachment to the foot by straps or stretchable bands, 2, 6, their direct connection points to the sole shown, and a textured underside design, 4, to deter ground or floor slippage.

Those versed in the art will appreciate that changes and emendations can be made to the embodiments and descriptions herein without departing from the spirit of the present innovation. All such alternatives and alterations are intended to be subsumed by the claims stated herein.

I claim:

1. A footwear device for supporting a wearer's foot when shoeless, the device to be worn when walking or standing indoors or out; the footwear device comprising:
   a) a raised midsole element, tapered at its longitudinal ends,
   b) wherein the footwear device does not support the wearer's heel, nor toes;
   c) wherein an upper surface of the midsole element is textured to resist epidermal slipping;
   d) wherein a lower surface of the midsole element comprises treading to provide ground traction,
   e) a plurality of straps providing lateral attachment of the midsole element to the wearer's foot;
   f) a fastener operably configured to connect the straps to each other above the sole of the wearer's foot; and
   g) wherein at least at the longitudinal median of the footwear device, the upper surface of the midsole element is raised at each lateral side of the midsole element above the lateral center of the upper surface of the midsole element.

2. The footwear device as recited in claim 1 wherein the midsole element and the plurality of straps are formed as a unitary structure.

3. The footwear device as recited in claim 1 wherein the midsole element is thicker in a vertical direction at the raised portions than the remainder of the midsole element.

4. The footwear device as recited in claim 1 wherein the footwear device is symmetric about a plane through a lateral median axis to allow the footwear device to be worn on the left or right foot.

\* \* \* \* \*